United States Patent [19]

Blum

[11] Patent Number: 5,105,823
[45] Date of Patent: Apr. 21, 1992

[54] SHIELDED REPLACEABLE LANCET BLADE ASSEMBLY

[76] Inventor: Alvin S. Blum, 2350 Del Mar Pl., Fort Lauderdale, Fla. 33301

[21] Appl. No.: 505,151

[22] Filed: Apr. 5, 1990

[51] Int. Cl.[5] ............................................. A61B 17/34
[52] U.S. Cl. .................................. 128/754; 606/171; 606/181; 606/182
[58] Field of Search .................. 604/198, 197, 263; 128/753, 754, 637, 751; 606/172, 182, 181, 167, 171

[56] References Cited

U.S. PATENT DOCUMENTS

| | | | |
|---|---|---|---|
| 4,517,978 | 5/1985 | Levin et al. | 128/314 |
| 4,637,403 | 1/1987 | Garcia | 606/182 |
| 4,731,059 | 3/1988 | Wanderer | 604/198 |
| 4,817,603 | 4/1989 | Turner | 606/182 |
| 4,840,619 | 6/1989 | Hughes | 604/198 |
| 4,927,018 | 5/1990 | Yang | 604/198 |

Primary Examiner—Ruth S. Smith
Assistant Examiner—Robert L. Nasser, Jr.
Attorney, Agent, or Firm—Alvin S. Blum

[57] ABSTRACT

A lancet blade assembly for an automatic, spring-loaded skin puncturing instrument provides shielding to the point of a replaceable blade during insertion of the blade into the instrument. It provides free movement of the blade during the puncture operation. After use, the assembly provides shielding of the point during removal. The assembly securely holds the blade with point protected before use and after discarding to prevent accidental puncture with a blood-contaminated blade.

8 Claims, 2 Drawing Sheets

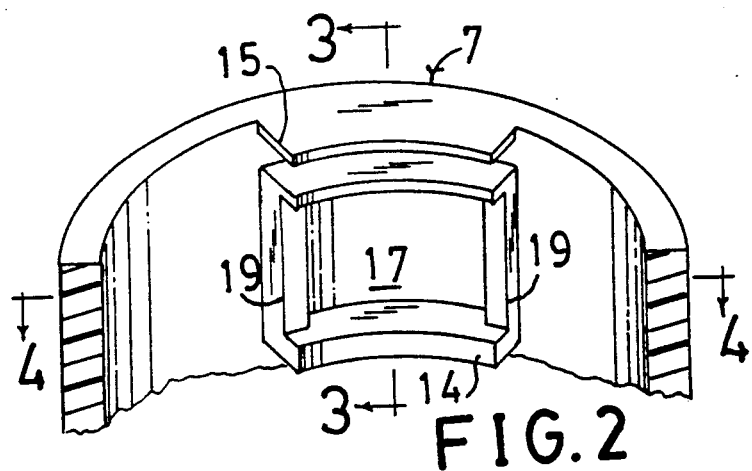
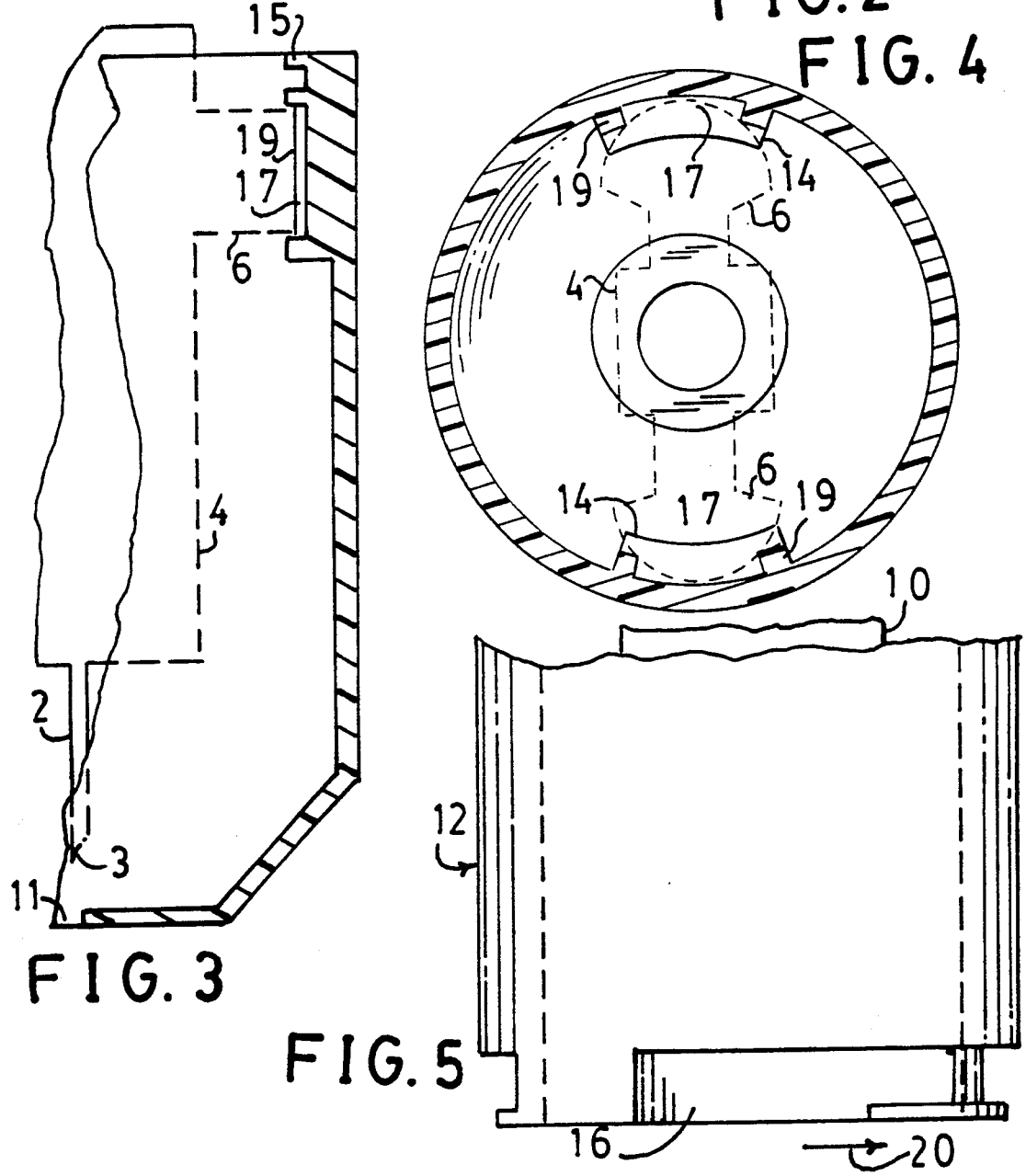
FIG. 2
FIG. 4
FIG. 3
FIG. 5

SHIELDED REPLACEABLE LANCET BLADE ASSEMBLY

This invention relates to sharp pointed blades and more particularly to lancet blades with protective shielding to prevent accidental puncturing during blade removal in a lancet driving apparatus.

BACKGROUND OF THE INVENTION

It is often necessary to examine a small drop of blood for clinical analysis. Hand-held disposable lancets are the simplest and cheapest implements for skin puncture to get the drop. Many automatic, spring-loaded devices that drive a replaceable and disposable blade have been developed to provide more consistent results with less pain. The blades must be removed and disposed of after use when they are contaminated with the blood of a patient. Generally, the point is covered by a nose cone or shield through which the point momentarily protrudes during puncturing. The blade then retracts. To remove and replace the blade, the nose cone or shield must first be removed and then the operator must extend his fingers past the point to grasps the shaft and pull it free.

When used by a diabetic for self-monitoring of blood glucose, there is discomfort, but no danger from accidental puncture during removal. However, when a clinical operator uses the device to sample a patient, the operator is exposed to life-threateningly infection if accidentally punctured during removal and disposal of a contaminated blade.

Many of the instruments employ a needle embedded in a plastic mount. The plastic mount has an extension that covers and protects the point before installation. After mounting the blade in the instrument the extension is twisted off before the nose cone is installed to cover the point. Consequently, the point is protected before use and the operator is protected against accidental puncture by the unused blade. The operator is unprotected from the used point after the nose cone is removed as is anyone who may come in contact with the point after use such as a trash handler.

SUMMARY OF THE INVENTION

It is accordingly an object of the invention to provide a lancet blade assembly for use in a blood sampling instrument that provides means for protecting the operator from accidental puncture with the blade. It is yet another object to provide means for protecting the point before use and after discarding. It is yet another object to provide a blade that is more effective in causing bleeding with minimal discomfort.

The invention includes an elongate blade with a sharp point at one end and a base that is not radially symmetrical. The base is arranged to removably engage the end of a reciprocating blade holder. The blade has an intermediate portion with laterally extending cone-engaging members. The nose cone has an interior with blade-engaging elements for removably engaging the cone-engaging members of the blade. With the cone free of the instrument and a blade engaged within, the case is pushed onto the instrument to seat the base of the blade on the end of the reciprocating blade holder. The cone is then rotated from a first to a second position. This action secures the cone to the instrument. Because the unsymmetrical base of the blade cannot rotate in its seat on the holder, the cone rotates relative to the blade. This action disengages the cone-engaging members of the blade from the cone. The blade is then free to reciprocate when driven by the holder during the puncturing operation. In the puncturing operation, the blade holder with its blade are momentarily driven forward relative to the housing and then promptly retracted so that the sharp point of the blade momentarily extends beyond the nose cone and into the skin before retracting within the nose cone. This puncturing operation is well known in lancet devices of the art and is generally spring driven. The needles or blades are solid, not hollow, so that blood collects on the skin after the blade is removed. After use, the cone is rotated from the second position to the first position. This frees the cone from the instrument and also causes the needle-engaging elements on the interior of the cone to engage the cone-engaging members of the blade so that the blade is securely held within the cone when the blade base is pulled from its seat on the reciprocating blade holder. The contaminated point of the blade is now safely covered by the cone for disposal.

These and other objects, advantages and features of the invention will be better understood by consideration of the detailed description in conjunction with the drawings.

BRIEF DESCRIPTION OF THE DRAWINGS

FIG. 2 is a perspective view of a portion of the nose cone showing blade-engaging feature.

FIG. 3 is a sectional view taken through line 3—3 of FIG. 2.

FIG. 4 is a sectional view taken through line 4—4 of FIG. 2.

FIG. 5 is a front elevation view of a portion of the housing showing a cone securing feature.

DETAILED DESCRIPTION OF THE PREFERRED EMBODIMENT

Figure 1:
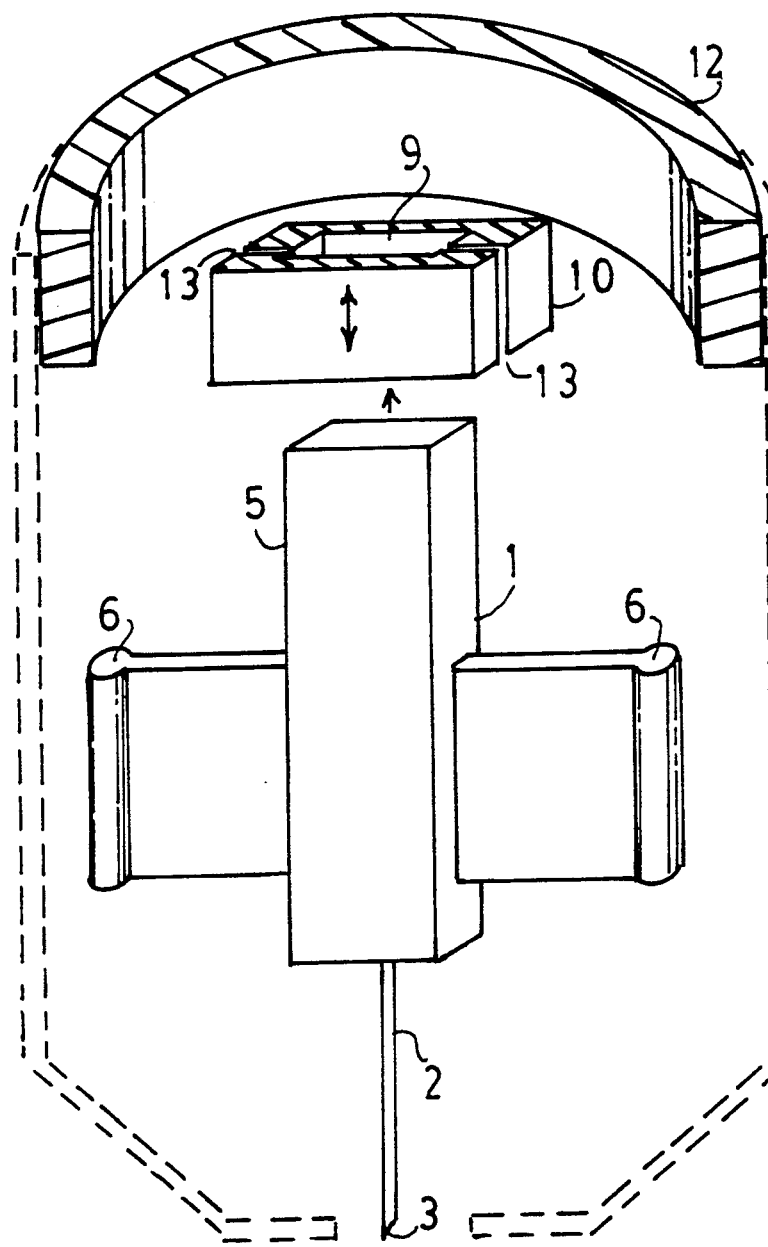
FIG. 1 is a perspective view of a lancet blade of the invention with nose cone shown in phantom.

Referring now first to FIG. 1, a lancet blade 1 includes a said needle 2 with a sharp point 3 embedded in a plastic base 4 having a rectangular body 5 and flexible wings 6 for removably engaging the nose cone 7, shown here in phantom. The rectangular body 5 of the blade fits snugly into the rectangular recess 9 in the lancet holder 10 which is of the type well known in the art that is spring driven in a down and up rapid motion relative to the housing 12 while holding the blade. The blade on its down stroke extends through hole 11 in the nose cone momentarily. The nose cone 7 fits securely on the end of the housing 12 that encircles the holder 10. Slots 13 in holder give it a springy holding action. Only the lower ends of holder 10 and housing 12 of the lancet driver device are shown.

Figure 6:
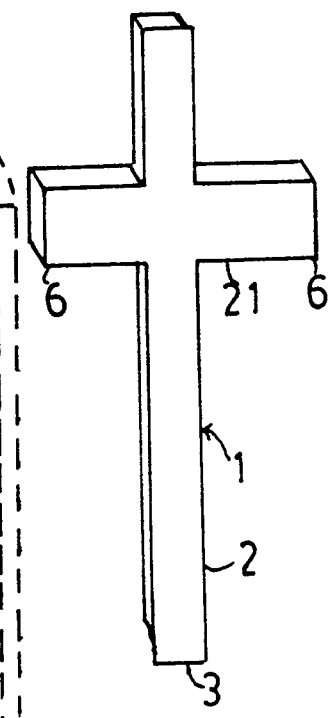
FIG. 6 is a perspective view of a lancet blade of the invention.

Referring now to FIGS. 2–5, nose cone 7 has two diametrically opposed projections 14 extending radially inward from the inside surface. The projections also include lugs 15 that fit into grooves 16 on exterior wall at the end of housing 12. This groove extends circumferentially partially around the wall of housing 12 so that after nose cone 7 is rotated, the lugs 15 slide around in groove 16 and lock the nose cone 7 securely in place in a manner well known in the art as exemplified by the bayonet type connectors in electronic art. The projections 14 provide a rectangular wall around a central space 17. The rectangular wall has two lower sides 19. When the nose cone 7 is ready for installation on the housing 12, the lancet is securely enclosed within the cone, with wings 6 held in place in central spaces 17. In this position, the rectangular body 5 of the blade 1 will be arranged to fit into the rectangular recess 9 in blade holder 10 (FIG. 1) when the lugs 15 are arranged to fit into grooves 16. When the nose cone is then rotated in the direction of arrow 20, the blade 1 is prevented from rotating by holder 10. The wings 6 will flex and ride over the lower side walls 19 of projection 14 freeing the blade from any connection to the nose cone. The blade is now free to reciprocate under the diving action of holder 10 in manner well known in the art. After the skin puncture is made, the nose cone is rotated in a direction opposite arrow 20 back to its original position. This will cause each wing 6 to once again be engaged within space 17 framed by the walls of projection 14. And the nose cone can be removed by simply pulling it downward. This action also pulls the blade 1 out of holder 10. The nose cone with the blade and its contaminated point completely enclosed therein may now be discarded without fear of accidental puncture. The nose cones can be provided with a sterile blade engaged within each one for single use. Alternatively, sterile blades may be furnished in a package with the base 5 of the blade held in place so that it cannot rotate. The blade is picked up by placing a nose cone over it and rotating it until the wings on the blade are engaged by the projections 14 and secured within spaces 17. The nose cone may then be pulled out with the blade ready for use. FIG. 6 shows an alternative embodiment of a blade 1 of the invention. The straight needle portion 2 is formed from a flat ribbon of metal whose end is ground to a sharp chisel point 3. The wings 6 are formed from a cross member 21 fastened to the needle shaft.

Figure 7:
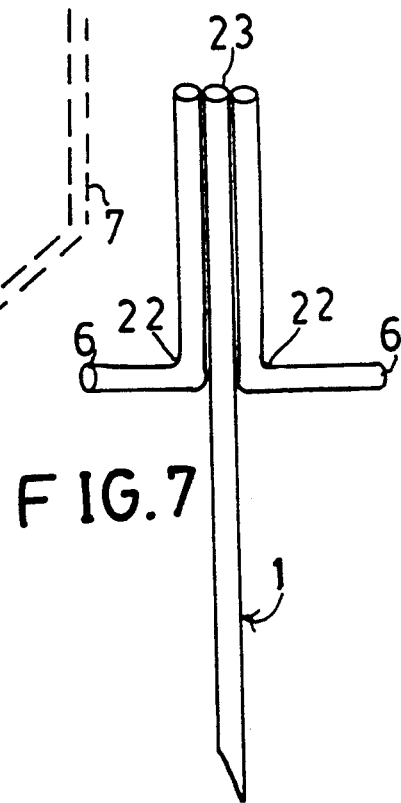
FIG. 7 is a perspective view of a lancet blade of the invention.

FIG. 7 shows an alternative embodiment of the blade 1 of the invention. The wings 6 are formed by attaching angle members 22 to the needle shaft. This also provides a base 23 that is not radially symmetrical so that it will not rotate when held in holder 10.

The above disclosed invention has a number of particle features which should preferably be employed in combination although each is useful separately without departure from the scope of the invention. While I have shown and described the preferred embodiments of my invention, it will be understood that the invention may be embodiment otherwise than as herein specifically illustrated or described, and that certain changes in the form and arrangement of parts and the specific manner of practicing the invention may be made within the underlying idea or principles of the invention within the scope of the appended claims.

I claim:

1. A device for puncturing the skin having a reciprocating driving mechanism for moving a blade mounting means with a skin puncturing lancet in a momentary extending and retracting motion relative to a housing enclosing said mechanism, comprising:
   a) an elongate blade means for skin puncturing, said blade means having a first end, an intermediate portion and a sharp, skin-puncturing second end, said first end having a radially asymmetrical shape and said intermediate portion having at least one laterally extending shield-engaging means;
   b) a blade driving mechanism for moving said blade means in a momentary extending and retracting, non-rotating reciprocating motion, and blade mounting means for removably mounting said blade means at said first end thereof onto said driving mechanism;
   c) housing means for enclosing said driving mechanism and said mounting means, whereby said reciprocating motion momentarily extends and retracts said blade means relative to said housing means;
   d) shield means for covering said second end of said blade means when said blade means is retracted, and exposing said second end of said blade means when said blade means is momentarily extended, said shield means provided with housing means, said shield means further including blade-engaging means for removably engaging said shield-engaging means of said blade means;
   e) said blade means being securely engaged by said shield means with said sharp, second end held within said shield means by interaction of said shield engaging means with said blade engaging means in a first operating condition for safe handling and disposal of said blade means and said shield means in combination when said shield means is not secured to said housing means; and
   f) said blade means being mounted onto said driving mechanism and disengaged from said shield means to permit translatory motion of said blade means relative to said shield means in a a second operation condition when said shield means is secured to said housing means by said housing securing means.

2. The device according to claim 1, in which said blade-engaging means is arranged to engage said shield-engaging means when said shield means is rotated in a first direction relative to said housing means and to disengage said shield-engaging means when said shield means is rotated in a second direction and said shield means is arranged to be secured to said housing means when said shield means is applied to said housing means and rotated in said second direction and said shield means is arranged to be unsecured from said housing means when said shield means is rotated in said first direction.

3. A shielded lancet for a conventional lancet driving device having a lancet holder, a housing and a reciprocating mechanism for momentarily extending and then retracting said lancet holder and a lancet relative to said housing, said shielded lancet comprising:
   a) an elongate blade means for skin puncturing, said blade means having a first end, an intermediate portion and a sharp, skin-puncturing second end, said first end having a radially asymmetrical shape and said intermediate portion having at least one laterally extending shield-engaging means; and
   b) shield means for covering said second end of said blade means when said blade is retracted, said shield means provided with housing securing means adapted to be removably attached to said housing, said shield means further including blade-engaging means for removably engaging said shield-engaging means;
   c) said blade means being securely engaged by said shield means with said sharp, second end held within said shield means by interaction of said shield engaging means with said blade engaging means in a first operating condition for safe handling and disposal of said blade means and said shield means in combination when said shield means is not attached to said housing; and d) said blade means being disengaged from said shield means to permit translatory motion of said blade means relative to said shield means in a a second operating condition when said shield means is secured to said housing by said housing securing means.

4. The shielded lancet according to claim 3, in which said blade-engaging means is arranged to engage said shield-engaging means when said shield means is rotated in a first direction relative to said blade means and to disengage said shield-engaging means when said shield means is rotated in a second direction and said shield means is arranged to be secured to a housing when said shield means is applied to said housing and rotated in said second direction and said shield means is arranged to be unsecured from said housing when said shield means is rotated in said first direction.

5. A shielded blade assembly for a conventional power-driven skin lancing device that holds a replaceable blade at the base in a blade driver, that drives the blade in a momentary to and fro rectilinear motion relative to a blade driver housing, advances said blade beyond a shield in a first, forward skin puncturing motion and then in a second, backward motion to a retraced position wherein the point is surrounded on its sides by said shield, said shielded blade assembly comprising:
 a) a blade having an elongate shaft with a sharp first end and a base means at a second end, said base means adapted for removably securing said blade to said blade driver;
 b) shield means for surrounding at least a portion of said shaft and said first end when said blade is in said retracted position, said shield means including attachment means adapted for removably attaching said shield means to said blade driver housing; and
 c) blade engaging means connected to said shield means for securely connecting said blade to said shield means in a first mode of operation in which said blade is in a retracted position and said base means is accessible for securing to said blade driver for use and said base means is removable from said blade driver for discarding by holding the shield means without danger of exposure to said sharp first end during insertion, removal and discarding, said blade engaging means having a second mode of operation in which said blade is disengaged from said shield means and said shield means is attached by said attachment means to said blade driver housing said blade engaging means being operative by manual movement of said shield means to change between first and second modes of operation, said blade being movable in a translatory motion relative to said shield means in said second mode of operation and being non-movable in a translatory motion relative to said shield means in said first mode of operation.

6. The device according to claim 1, in which said skin-puncturing second end of said blade means is comprised of a solid material with a sharp end.

7. The shielded lancet according to claim 3, in which said sharp, skin-puncturing second end of said blade means is comprised of a solid material with a sharp end.

8. The blade assembly according to claim 5, in which said first end of said blade is comprised of a solid material with a sharp end.

* * * * *